United States Patent
Beuvink et al.

(10) Patent No.: US 7,749,698 B2
(45) Date of Patent: Jul. 6, 2010

(54) P53 WILD-TYPE AS BIOMARKER FOR THE TREATMENT WITH MTOR INHIBITORS IN COMBINATION WITH A CYTOTOXIC AGENT

(75) Inventors: Iwan Beuvink, Biel-Benken (CH); Anne Boulay, Blotzheim (FR); Heidi Lane, Biel-Benken (CH); Terence O'Reilly, Basel (CH); George Thomas, Wyoming, OH (US)

(73) Assignee: Novartis AG, Basel (CH)

( * ) Notice: Subject to any disclaimer, the term of this patent is extended or adjusted under 35 U.S.C. 154(b) by 637 days.

(21) Appl. No.: 10/590,406

(22) PCT Filed: Feb. 22, 2005

(86) PCT No.: PCT/EP2005/001849

§ 371 (c)(1),
(2), (4) Date: Oct. 4, 2006

(87) PCT Pub. No.: WO2005/080593

PCT Pub. Date: Sep. 1, 2005

(65) Prior Publication Data

US 2008/0194613 A1   Aug. 14, 2008

Related U.S. Application Data

(60) Provisional application No. 60/546,856, filed on Feb. 23, 2004.

(51) Int. Cl.
*C12Q 1/68* (2006.01)
*G01N 33/53* (2006.01)

(52) U.S. Cl. .......................................... 435/6; 435/7.1

(58) Field of Classification Search ....................... None
See application file for complete search history.

(56) References Cited

U.S. PATENT DOCUMENTS 6,521,407 B1   2/2003   Warenius et al.

FOREIGN PATENT DOCUMENTS

WO   02/066019   8/2002

OTHER PUBLICATIONS

Huang et al., "Mechanisms of Resistance to Rapamycins", Drug Resistance Updates, vol. 4, No. 6, pp. 378-391 (2001).
Hosoi et al., "Rapamycin Causes Poorly Reversible Inhibition of mTOR and Induces P53-Independent Apoptosis in Human Rhabbomyosarcoma Cells", Cancer Research, vol. 59, No. 4, pp. 886-894 (1999).
Huang et al., "P53/P21CIPL Cooperate in Enforcing Rapamycin-Induced G1 Arrest and Determine the Cellular Response to Rapamycin", Cancer Research, vol. 61, pp. 3373-3381 (2001).
Hosoi et al., "Studies on the Mechnism of Resistance to Rapamycin in Human Cancer Cells", Molecular Pharmacology, vol. 54, pp. 815-824 (1998).
Tian et al., "P21WAF1/CIP1 Antisense Therapy Radiosensitizes Human Colon Cancer by Converting Growth Arrest to Apoptosis", Cancer Research, vol. 60, No. 3, pp. 679-684 (2000).

*Primary Examiner*—James Martinell
(74) *Attorney, Agent, or Firm*—Lydia T. McNally

(57) ABSTRACT

Provided are biomarkers for determining the sensitivity of proliferative diseases such as cancer to therapeutic agents, in particular mTOR inhibitors in combination with a cytotoxic agent, in particular a cytotoxic agent which damages or affects the integrity of DNA.

5 Claims, No Drawings

SEQUENCE LISTING

<160> NUMBER OF SEQ ID NOS: 5

<210> SEQ ID NO 1
<211> LENGTH: 19
<212> TYPE: DNA
<213> ORGANISM: Artificial
<220> FEATURE:
<223> OTHER INFORMATION: Primer sequence

<400> SEQUENCE: 1
gcatcttatc cgagtggaa                                                19

-continued

```
<210> SEQ ID NO 2
<211> LENGTH: 21
<212> TYPE: DNA
<213> ORGANISM: Artificial
<220> FEATURE:
<223> OTHER INFORMATION: Primer sequence

<400> SEQUENCE: 2
gcggctgccg gaatttacct t                                              21

<210> SEQ ID NO 3
<211> LENGTH: 19
<212> TYPE: DNA
<213> ORGANISM: Artificial
<220> FEATURE:
<223> OTHER INFORMATION: Primer sequence

<400> SEQUENCE: 3
ggaagactcc agtggtaat                                                 19

<210> SEQ ID NO 4
<211> LENGTH: 19
<212> TYPE: DNA
<213> ORGANISM: Artificial
<220> FEATURE:
<223> OTHER INFORMATION: Primer sequence

<400> SEQUENCE: 4
gatattgaac aatggttca                                                 19

<210> SEQ ID NO 5
<211> LENGTH: 19
<212> TYPE: DNA
<213> ORGANISM: Artificial
<220> FEATURE:
<223> OTHER INFORMATION: Primer sequence

<400> SEQUENCE: 5
gtggacagcg agcagctga                                                 19
```

P53 WILD-TYPE AS BIOMARKER FOR THE TREATMENT WITH MTOR INHIBITORS IN COMBINATION WITH A CYTOTOXIC AGENT

This application claims benefit of U.S. Provisional Application No. 60/546,856, filed Feb. 23, 2004, which in its entirety is herein incorporated by reference.

The present invention relates to biomarkers for determining the sensitivity of proliferative diseases such as cancer to therapeutic agents, in particular mTOR inhibitors in combination with a cytotoxic agent.

A number of mTOR inhibitors have potent antiproliferative properties which make them useful for cancer chemotherapy, particularly of solid tumors, especially of advanced solid tumors. mTOR inhibitors have also been combined with certain cytotoxic agents to further improve the efficiency of the treatment or to reduce the side-effects, e.g. as disclosed in WO 02/66019. However there is still a need for more targeted use of a combined therapy based on mTOR inhibitors, which requires identification of patients which are likely to respond to treatment with such combined agents. Accordingly there is a need for biomarkers useful in e.g. clinical tests, which are capable of predicting responsiveness of a benign or malignant proliferative disease, e.g. a tumor in a patient, to treatment with an mTOR inhibitor in association with a cytotoxic agent.

It has surprisingly been found that the presence of a wild-type p53 tumor suppressor gene (otherwise also known as the TP53 gene) is a useful biomarker which is predictive of sensitivity of proliferative diseases to treatment with a combination of an mTOR inhibitor with a cytotoxic agent. In particular, it has been found that the presence of a wild-type p53 gene in human cancer cell lines correlates well with increased cell killing/programmed cell death/apoptosis resulting from treatment with an mTOR inhibitor in combination with a cytotoxic agent that damages or affects the integrity of DNA. Hence, mTOR inhibitors combined with a cytotoxic agent are more likely to show a more significant antiproliferative/cell killing effect when used to treat cancer cells which retain wild-type p53. The p53 protein (encoded by the TP53 gene) is a tumor-suppressor which plays a major role in the regulation of cell cycle arrest, senescence, differentiation and programmed cell death/apoptosis in mammalian cells. In particular, the p53 pathway induces cell cycle arrest and/or apoptosis in mammalian cells exposed to stress (e.g. DNA damage, oncogenic stress, hypoxia, lack of survival signals). Mutations in TP53 occur in about half of all human cancers, and the ability to induce a p53 response is compromised in many cancer cells (Vousden and Lu, Nature Reviews, 2002, 2:594-604). The sequence of human p53 (mRNA [coding sequence; 1182 nucleotides] and protein [393 amino acids]) is available under GenBank accession numbers NM 000546 or P04637. The complete sequence of the human TP53 gene is available under GenBank accession number U94788.

Accordingly, the present invention is based on the determination of the presence of a wild-type p53 (TP53) gene in cells which are prone to abnormal proliferation.

The present invention provides in one aspect the use of the presence of wild-type p53 (TP53) gene (as opposed to the absence, deficiency or deletion of the p53 [TP53] gene or the presence of a mutated p53 [TP53] gene) as a biomarker for determining the sensitivity of a proliferative disease to treatment with an mTOR inhibitor in combination with a cytotoxic agent.

By wild-type p53 (TP53) gene is meant not only the introns and exons but also regulatory regions associated with, and physically close to, the introns and exons, particularly those 5' to the 5'-most exon. It includes e.g. the full length DNA sequence of the natural gene and optionally nucleotide substitutions (including inversions), insertions and deletions of codons, provided that it expresses the wild-type p53 protein or a functional equivalent thereof, e.g. a functional p53 protein retaining its cell apoptosis-inducing properties. Conversely, absence, deficiency, deletion or mutation of the p53 (TP53) gene is meant for genetic and epigenetic changes e.g. amplification, methylation, polymorphisms, nucleotide mutations, deletions, inversions or translocations and loss of heterozygosity (LOH) which results in loss of p53 (TP53) gene expression or expression of a mutated gene which e.g. results in expression of a mutated p53 protein which no longer retains cell apoptosis-inducing properties.

In a further aspect the invention provides a method for determining the sensitivity of a proliferative disease in a subject to treatment with an mTOR inhibitor in combination with a cytotoxic agent, comprising determining p53 (TP53) status (wild-type versus mutant or deficient/absent) in a sample derived from the subject.

In another aspect the invention provides a method of selecting subjects suffering from a proliferative disease for treatment with an mTOR inhibitor in association with a cytotoxic agent, comprising determining the sensitivity of the proliferative disease to the combined treatment in each subject by a method as described above, and selecting those subjects retaining a wild-type p53 (TP53) gene for said combined treatment.

The term "mTOR inhibitor" as used herein includes, but is not limited to rapamycin (sirolimus) or a derivative thereof. Rapamycin is a known macrolide antibiotic produced by *Streptomyces hygroscopicus*. Suitable derivatives of rapamycin include e.g. compounds of formula A

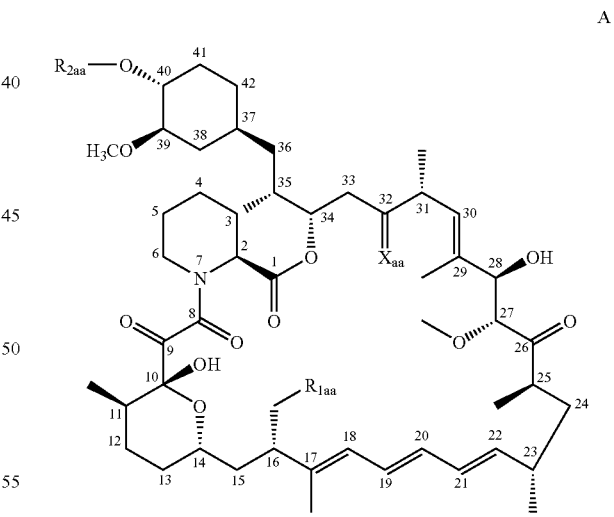

wherein $R_{1aa}$ is $CH_3$ or $C_{3-6}$alkynyl, $R_{2aa}$ is H or —$CH_2$—$CH_2$—OH, 3-hydroxy-2-(hydroxymethyl)-2-methyl-propanoyl or tetrazolyl, and $X_{aa}$ is =O, (H,H) or (H,OH)

provided that $R_{2aa}$ is other than H when $X_{aa}$ is =O and $R_{1aa}$ is CH3.

or a prodrug thereof when $R_{2aa}$ is —CH$_2$—CH$_2$—OH, e.g. a physiologically hydrolysable ether thereof.

Compounds of formula A are disclosed e.g. in WO 94/09010, WO 95/16691, WO 96/41807, U.S. Pat. No. 5,362, 718 or WO 99/15530 which are incorporated herein by reference. They may be prepared as disclosed or by analogy to the procedures described in these references.

Representative rapamycin derivatives of formula I are e.g. 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxymethyl)-2-methylpropanoate]-rapamycin (also called CCI779) or 40-epi-(tetrazolyl)-rapamycin (also called ABT578). A preferred compound is e.g. 40-0-(2-hydroxyethyl)-rapamycin disclosed in Example 8 in WO 94/09010, or 32-deoxorapamycin or 16-pent-2-ynyloxy-32(S)-dihydro-rapamycin as disclosed in WO 96/41807. Rapamycin derivatives may also include the so-called rapalogs, e.g. as disclosed in WO 98/02441 and WO01/14387, e.g. AP23573, AP23464, AP23675 or AP23841. Further examples of a rapamycin derivative are those disclosed under the name TAFA-93 (a rapamycin prodrug), biolimus-7 or biolimus-9.

In each case where citations of patent applications or scientific publications are given, the subject-matter relating to the compounds is hereby incorporated into the present application by reference. Comprised are likewise the pharmaceutically acceptable salts thereof, the corresponding racemates, diastereoisomers, enantiomers, tautomers as well as the corresponding crystal modifications of above disclosed compounds where present, e.g. solvates, hydrates and polymorphs, which are disclosed therein. The compounds used as active ingredients in the combinations of the invention can be prepared and administered as described in the cited documents, respectively.

The term "cytotoxic agent" as used herein is an agent which is harmful to cell structure and function, e.g. that damages or affects the DNA integrity, and may ultimately cause cell death, e.g. a antineoplastic drug, for instance a microtubule active agent or especially a drug which damages DNA, for example an antineoplastic antimetabolite, a platin compound, an alkylating agent or a topoisomerase I or II inhibitor. The term "cytotoxic agent" also includes an irradiation treatment which causes DNA damage, e.g ionizing radiation, e.g. radioactive iodine. Such irradiation treatment may also be combined with the cytotoxic agent therapy. The term "cytotoxic agent" also includes one, two or more cytotoxic agents which may be administered in the form of a "cocktail" therapy.

The term "topoisomerase I inhibitor" as used herein includes, but is not limited to topotecan, irinotecan, gimatecan, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR™. Topotecan can be administered, e.g., in the form as it is marketed, e.g. under the trademark HYCAMTIN™.

The term "topoisomerase II inhibitor" as used herein includes, but is not limited to the anthracyclines such as doxorubicin (including liposomal formulation, e.g. CAELYX™), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS™. Teniposide can be administered, e.g. in the form as it is marketed, e.g. under the trademark VM 26-BRISTOL™. Doxorubicin can be administered, e.g. in the form as it is marketed, e.g. under the trademark ADRIBLASTIN™. Epirubicin can be administered, e.g. in the form as it is marketed, e.g. under the trademark FARMORUBICIN™. Idarubicin can be administered, e.g. in the form as it is marketed, e.g. under the trademark ZAVEDOS™. Mitoxantrone can be administered, e.g. in the form as it is marketed, e.g. under the trademark NOVANTRON™.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof. Paclitaxel may be administered e.g. in the form as it is marketed, e.g. TAXOL™. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agent" as used herein includes, but is not limited to cyclophosphamide, ifosfamide, melphalan or nitrosourea (BCNU or Gliadel™). Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "antineoplastic antimetabolite" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD1694 (RALTITREXED™), LY231514 (ALIMTA™), LY264618 (LOMOTREXOL™) and OGT719. Capecitabine can be administered, e.g., in the form as it is marketed, e.g. under the trademark XELODA™. Gemcitabine can be administered, e.g., in the form as it is marketed, e.g. under the trademark GEMZAR™.

The term "platin compound" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The proliferative disease may be a benign or malignant proliferative disease, e.g. benign prostatic hyperplasia, or a neoplastic disease, preferably a malignant proliferative disease, e.g. a cancer, e.g. tumors and/or metastasis (where ever located), e.g. brain and other central nervous system tumors (eg. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-asso-ciated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, tumors of blood and lymphatic system (e.g. Hodgkin's disease, Non-Hodgkin's lymphoma, Burkift's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

The term cytotoxic agent may also, in case of a lymphatic or myeloid cancer, be e.g. busulfan, cytarabine, 6-thioguanine, fludarabine, hydroxyurea, procarbazine, bleomycin or methotrexate. Topoisomerase II inhibitors e,g. daunorubicin or idarubicin or, particularly, compounds which target, decrease or inhibit the activity of PDGFR or of c-Abl family members and their gene fusion products, e.g. imatinib, farnesyltransferase inhibitors, Ara-C, VP-16, Teniposide, Mitoxantrone, Carboplatin or midostaurine are preferred as cytotoxic agent in case of a lymphatic or myeloid cancer.

According to the method of the present invention, subjects suffering from such a proliferative disease can be screened in order to predict their sensitivity to a combined treatment of mTOR inhibitors with a cytotoxic agent. The method may be performed in vitro, e.g. on a sample of biological tissue derived from the subject. The sample may be any biological material separated from the mammalian body such as e.g. tissue, cell lines, plasma or serum, cell or tissue lysate, preferably tumor tissue.

The status of the p53 (TP53) gene is assayed in the biological sample by any technical means on the basis of e.g. DNA analysis for genetic and epigenetic changes e.g. DNA scanning for amplification, methylation, polymorphisms, nucleotide mutations (e.g. mutations of codons 175Arg, 245Gly, 248Arg, 249Arg, 273Arg, 282Arg and others) nucleotide deletions, inversions and/or translations and loss of heterozygosity (LOH). p53 (TP53) status is assayed in the biological samples by any technical means on the basis of e.g. RNA expression using for example the techniques of northern blotting or RT-PCR or on the basis of e.g. protein expression/ modifications using for example the technique of Western blotting, immunohistochemistry or ELISA, including immunoassays, immunoprecipitation and electrophoresis assays.

For example, antibodies specific for p53 protein or p53 post-translational modifications such as phosphorylation (e.g. phosphorylation of Ser46), ubiquitination or acetylation may be used in a standard immunoassay format to measure p53 protein/phosphorylation/ubiquitination/acetylation levels. ELISA (enzyme linked immunosorbent assay) type assays, immunoprecipitation type assays, conventional Western blotting assays and immunohistochemistry assays using e.g. monoclonal or polyclonal antibodies are also utilized to determine levels of p53 protein/post-translational modifications as a biomarker.

Polyclonal and monoclonal antibodies specific to p53 protein/post-translational modifications are produced in accordance with known immunization methods or are commercially available (e.g. Santa Cruz Biotechnology Inc catalogue #sc6253).

The p53 status may also be measured by two-dimensional (2-D) gel electrophoresis. 2-D gel electrophoresis is known in the art and typically involves isoelectric focusing (IEF) along a first dimension followed by SDS-PAGE (sodium dodecyl sulphate-polyacrylamide gel electrophoresis) along a second dimension. The resulting electropherograms are analyzed, for example, by immunoblot analysis using antibodies.

The present invention thus provides a method of screening subjects suffering from a proliferative disease in order to predict their responsiveness to a combined treatment with an mTOR inhibitor and a cytotoxic agent, comprising determining the p53 (TP53) status by a method as defined above.

In a further aspect, the present invention provides a method of treating a proliferative disease in a subject in need thereof, comprising determining the status of the p53 (TP53) gene or the level of p53 expression and/or post-translational modifications in a sample derived from the subject, by a method as described above, and treating the subject with an mTOR inhibitor in combination with a cytotoxic agent accordingly.

In an alternative embodiment, the present invention provides a method for enhancing the activity of a cytotoxic agent or for overcoming resistance to a cytotoxic agent in a subject in need thereof, comprising determining the status of the p53 (TP53) gene/expression in a sample derived from the subject, by a method as described above, and administering to said subject a therapeutically effective amount of an mTOR inhibitor, either concomitantly or sequentially with said cytotoxic agent.

p53 (TP53) status in a particular tissue from a subject, e.g. a sample of tumor tissue, may be compared with a control sample, e.g. a sample of normal tissue from a subject not suffering from the disease, or a sample of normal (i.e non-tumor) tissue from the same subject. The p53 (TP53) wild-type status level at which use of an mTOR inhibitor in association with a cytotoxic agent is indicated, is predictive of a beneficial therapeutic effect (i.e. an antiproliferative and/or increased cell killing effect) of a combined treatment of an mTOR inhibitor with a cytotoxic agent.

Moreover, the method may be used to aid selection of an appropriate dose of a cytotoxic agent and/or an mTOR inhibitor in order to individually optimise therapy for each patient. Depending on the p53 wild-type status in a patient, lower doses of the active ingredients of the combination can be used; for example, the dosages need not only often be smaller but may also be applied less frequently, or can be used in order to diminish the incidence of side-effects, while controlling the undesired proliferation. Factors for consideration in this context include the particular condition being treated, the particular mammal being treated, the clinical condition of the individual patient, the site of delivery of the active compounds, the particular type of the active compounds, the method of administration, the scheduling of administration, the severity of the condition and other factors known to medical practitioners.

The terms "combined treatment" or "in combination with" or "in association with" or the like as utilized herein are meant to encompass administration of the selected mTOR inhibitor and cytotoxic agent to a single patient, and are intended to include treatment regimens in which the agents are not necessarily administered by the same route of administration or at the same time. For example, the mTOR inhibitor and the cytotoxic agent may be administered to a patient as separate entities either simultaneously, concurrently or sequentially with no specific time limits, wherein such administration provides therapeutically effective levels of the two compounds in the body.

The therapeutically effective amount of each active component of the combination to be administered will be governed by considerations as mentioned above, and is the minimum amount necessary to prevent, ameliorate, or treat the disease. Such amount is preferably below the amount that is toxic to the host or which renders the host significantly more susceptible to infections.

Appropriate doses of an mTOR inhibitor are e.g. as disclosed in WO 02/66019, e.g. daily dosage rates of the order of ca. 0.1 to 30 mg, e.g. from ca. 0.05 to 20 mg active ingredient p.o., as a single dose or in divided doses or intermittent, e.g. once a week. Rapamycin or a derivative thereof, e.g. a compound of formula A, may be administered by any conventional route, in particular enterally, e.g. orally, e.g. in the form of tablets, capsules, drink solutions or parenterally, e.g. in the form of injectable solutions or suspensions, containing, for example, from about 0.1% to about 99.9%, preferably from about 1% to about 60%, of the active ingredient(s).

Topotecan may be administered to a human in a dosage range varying from about 1 to 5 mg/m$^2$ day. Irinotecan may be administered to a human in a dosage range varying from about 50 to 350 mg/m$^2$ day.

Paclitaxel may be administered to a human in a dosage range varying from about 50 to 300 mg/m$^2$ day. Docetaxel may be administered to a human in a dosage range varying from about 25 to 100 mg/m$^2$ day.

Cyclophosphamide may be administered to a human in a dosage range varying from about 50 to 1500 mg/m$^2$ day. Melphalan may be administered to a human in a dosage range varying from about 0.5 to 10 mg/m$^2$ day.

5-Fluorouracil may be administered to a human in a dosage range varying from about 50 to 1000 mg/m$^2$ day, e.g. 500 mg/m$^2$ day. Capecitabine may be administered to a human in a dosage range varying from about 10 to 1000 mg/m$^2$ day. Gemcitabine hydrochloride may be administered to a human in a dosage range varying from about 1000 mg/m$^2$/week.

Carboplatin may be administered to a human in a dosage range varying from about 200 to 400 mg/m$^2$ about every four weeks. Cisplatin may be administered to a human in a dosage range varying from about 25 to 75 mg/m$^2$ about every three weeks. Oxaliplatin may be administered to a human in a dosage range varying from about 50 to 85 mg/m$^2$ every two weeks.

Imatinib may be administered to a human in a dosage in the range of about 2.5 to 850 mg/day, more preferably 5 to 600 mg/day and most preferably 20 to 300 mg/day.

A preferred combination to be used in a method in accordance with the invention is e.g. a combination of rapamycin, 40-[3-hydroxy-2-(hydroxymethyl)-2-methylpropanoate]-rapamycin or 40-O-(2-hydroxyethyl) rapamycin with a cytotoxic agent such as gemcitabine or cisplatin. An alternative combination to be used in a method according to the invention is a combination in synergistic amounts of an mTOR inhibitor with a cytotoxic agent, e.g. gemcitabine or cisplatin, e.g. as disclosed above.

Preferably TP53 is the human gene.

Preferably the methods of the invention are performed on tumor cells presenting a p53 (TP53) wild-type status.

In a further embodiment, it has surprisingly been found that the increased cell killing/programmed cell death/apoptosis resulting from treatment with an mTOR inhibitor in combination with a cytotoxic agent in p53 (TP53) wild-type cells is associated with a strong attenuation of cytotoxic-induced upregulation of p21$^{Waf1/Cip1}$ (also known as CDKN1A, WAF1, CIP1, SDI1, CAP20, MDA-6, p21) protein expression, referred to hereafter as p21.

p21 is a member of the cip/kip family of cyclin kinase "inhibitors", which plays a role in allowing cell cycle transit as well as preventing apoptosis. In the context of the present invention, the function of p21 to arrest cell growth in response to stress signals, e.g. DNA damage, in response to activated p53 is well established. Indeed, it is postulated that increased p21 protein expression allows such stressed cells to survive, e.g. allowing the cell to complete the DNA repair process. Hence, attenuation of increased p21 expression in response to treatment with cytotoxics may promote cell killing/programmed cell death/apoptosis (Weiss, Cancer Cell, 2003, 4:425-429). The sequence of human p21 (mRNA [coding sequence: 495 nucleotides] and protein product [164 amino acids]) is available under GenBank accession number NM 000389, NM 078467 or AAH01935. The complete sequence of the human p21 gene is available under GenBank accession number NM 078467.

Furthermore, some cancer patients have increased total or cytosolic tumor p21 expression which has been linked to poor prognosis and poor response to chemotherapy (Weiss, supra). The assessment of the basal p21 expression in a cancer patient may also allow to select the patients for a specific chemotherapeutic treatment, e.g. based on mTOR therapy in combination with one or more cytotoxic agents and optionally radiotherapy.

Accordingly, the present invention further provides:

i. use of p21 as a biomarker for determining the sensitivity or response of a proliferative disease in a subject to treatment with an mTOR inhibitor in combination with a cytotoxic agent;

ii. a method of selecting subjects suffering from a proliferative disease for treatment with an mTOR inhibitor in combination with a cytotoxic agent, comprising determining the sensitivity of the proliferative disease to treatment with an mTOR inhibitor in combination with a cytotoxic agent in each subject by a method as described above, and selecting those subjects showing increased basal p21 expression for combination treatment;

iii. a method for determining the sensitivity or response of a proliferative disease in a subject to a treatment with an mTOR inhibitor, in combination with a cytotoxic agent, comprising determining in a sample derived from the subject the level of p21 expression before and/or after treatment with the cytotoxic agent alone and in combination with an mTOR inhibitor;

iv. a method for enhancing the activity of a cytotoxic agent or for overcoming resistance to a cytotoxic agent in a subject treated with said cytotoxic agent, comprising determining the level of p21 expression in a sample derived from the subject, by a method as described above, if p21 expression is upregulated after administration of a cytotoxic agent, administering to said subject a therapeutically effective amount of an mTOR inhibitor in combination with the cytotoxic agent, determining again the level of p21 expression in a new sample derived from the subject after the treatment with the combination of the mTOR inhibitor and the cytotoxic agent, and if p21 expression is downregulated, further treating the subject with the mTOR inhibitor either concomitantly or sequentially with said cytotoxic agent.

As already mentioned above, p21 protein levels may be determined as disclosed above for p53; however, instead of using antibodies specific to p53, it is understood to use an antibody specific for p21, e.g. a monoclonal or polyclonal antibody, e.g. as commercially available (e.g. Oncogene Research products, Clone EA10, catalogue #OP64).

The level found in a particular tissue from a subject, e.g. a sample of tumor tissue, may be compared with a control sample, e.g. a sample of normal tissue from a subject not suffering from the disease, or a sample of normal (i.e non-tumor) tissue from the same subject. A lack of or attenuation of the induction of p21 expression (when treated with an mTOR inhibitor in combination with a cytotoxic agent as compared to the induction observed with the cytotoxic agent alone) is predictive of a beneficial therapeutic effect (i.e. an antiproliferative/cell killing effect) of an mTOR inhibitor in combination with a cytotoxic agent. The assessment of the induction of p21 expression by the cytotoxic agent and/or of the reversing effect by the mTOR inhibitor on p21 expression level may also be useful to adapt the doses of the cytotoxic agent, e.g. to reduce the cytotoxic dose.

The present Examples illustrate the invention without any limitation.

EXAMPLE 1 p53 (TP53) wild-type human adenocarcinoma A549 (CCL-185) tumor cells (American Type Culture Collection, Rockville, Md., USA) are seeded at a density of $2 \times 10^3$ cells/100 µl per well in 96-well plates and incubated for 24 hours at 37° C. and 5% $CO_2$. Cells are incubated with suboptimal concentrations of gemcitabine (e.g. 5 to 17.5 nM) either in combination with 20 nM 40-O-(2-hydroxyethyl) rapamycin or with the vehicle-control DMSO for an additional 72 hours. YO-PRO dye (YO-PRO$^R$-1 iodide [491/509], cat #Y3603, Molecular Probes) is added to the cells and a Cytofluor II Fluorescence plate reader is used to determine cell death or cytotoxicity and, after cell lysis, the relative cell proliferation. In this assay, the mTOR inhibitor, e.g. 40-O-(2-hydroxyethyl) rapamycin, causes a statistically significant potentiation of the cell killing effect of suboptimal concentrations of gemcitabine (p<0.05; ANOVA with Tukey test). Similar results as disclosed above are obtained when using a p53 (PT53) wild-type cell line other than the human lung adenocarcinoma A549, e.g. human MCF7 breast carcinoma cells (HTB-22; American Type Culture Collection).

This procedure is repeated however with the use of p53 (TP53) mutated/deficient tumor cell lines, e.g. PC3M human prostate carcinoma cells (seeded at a density of $0.8 \times 10^3$ cells/100 µl) or MDA-MB231 human breast carcinoma cells (seeded at a density of $2 \times 10^3$ cells/100 µl; HTB-26; American Type Culture Collection). No striking or consistent potentiation of cell death is seen in p53 (TP53) mutated/deficient cell lines.

A549 cells are seeded at a density of $0.1 \times 10^6$ cells/10 ml per 10 cm plates and incubated for 24 hours at 37° C. and 5% $CO_2$. Cells are incubated with suboptimal concentrations of gemcitabine (e.g. 5 to 12.5 nM) either in combination with 20 nM 40-O-(2-hydroxyethyl) rapamycin or with the vehicle-control DMSO for an additional 72 hours. Cell extracts corresponding to 50 µg total protein are resolved by 8% SDS-PAGE electrophoresis and immunoblot analysis is performed using rabbit polyclonal antibodies raised against Poly (ADP-Ribose) Polymerase (PARP) (Cell Signalling Technology catalogue #9542). In this assay, the presence of the mTOR inhibitor, e.g. 40-O-(2-hydroxyethyl) rapamycin, causes increased PARP cleavage (a marker of apoptosis) at suboptimal gemcitabine concentrations (as compared to gemcitabine or the mTOR inhibitor alone at the same concentrations). This confirms the above results that, in the p53 (TP53) wild-type A549 cells, the presence of the mTOR inhibitor results in higher levels of cell death at suboptimal gemcitabine concentrations.

EXAMPLE 2 p53 (TP53) wild-type human lung adenocarcinoma A549 cells are seeded at a density of $5 \times 10^3$ cells/100 µl per well in 96-well plates and incubated for 24 hours at 37° C. and 5% $CO_2$. Cells are incubated with suboptimal concentrations of cisplatin (e.g. 3 to 10 µg/ml) either in combination with 20 nM 40-O-(2-hydroxyethyl) rapamycin or with the vehicle-control DMSO for an additional 24 hours. The YO-PRO® assay is performed as above to determine cell death or cytotoxicity and, after cell lysis, the relative cell proliferation. In this assay, the mTOR inhibitor, e.g. 40-O-(2-hydroxyethyl) rapamycin, causes a statistically significant potentiation of the cell killing effect of suboptimal concentrations of cisplatin (p<0.05; ANOVA with Tukey test). Subsequent analysis using two-way ANOVA indicates that the interaction between RAD001 and cisplatin was highly significant (p<0.001). Similar results as disclosed above are obtained when using a p53 (PT53) wild-type cell line other than the human lung adenocarcinoma A549, e.g. human MCF7 breast carcinoma cells. In the latter case, incubation with compounds is for 30 hours.

This procedure is repeated however with the use of p53 (TP53) mutated/deficient tumor cell lines, e.g. PC3M (seeded at a density of $3 \times 10^3$ cells/100 µl) or DU145 (seeded at a density of $5 \times 10^3$ cells/100 µl:HTB-81; American Type Culture Collection). The incubation with compounds in this case is 22 hours for DU145 or 30 hours for PC3M. No striking or consistent potentiation of cell death is seen in p53 (TP53) mutated/deficient cell lines.

A549 cells are seeded at a density of $0.1 \times 10^6$ cells/10 ml per 10 cm plates and incubated for 24 hours at 37° C. and 5% $CO_2$. Cells are incubated with suboptimal concentrations of cisplatin (e.g. 0.5 to 4 µg/ml) either in combination with 20 nM 40-O-(2-hydroxyethyl) rapamycin or with the vehicle-control DMSO for an additional 24 hours. Cell extracts corresponding to 50 µg total protein are resolved on 8% SDS-PAGE electrophoresis and immunoblot analysis is performed using rabbit polyclonal antibodies raised against Poly (ADP-Ribose) Polymerase (PARP) and p53. In this assay, the presence of the mTOR inhibitor, e.g. 40-O-(2-hydroxyethyl) rapamycin, causes increased PARP cleavage (a marker of apoptosis) at suboptimal cisplatin concentrations (as compared to cisplatin or the mTOR inhibitor alone at the same concentrations). This confirms the above results that, in the p53 (TP53) wild-type A549 cells, the presence of the mTOR inhibitor results in higher levels of cell death at suboptimal cisplatin concentrations.

The p53 (TP53) status predicts sensitivity of e.g. a tumor in a subject to a combination of an mTOR inhibitor with a cytotoxic agent. p53 status can be assessed using DNA, RNA or protein obtained from tumor tissue as disclosed in order to predict likely responsiveness to a combination of an mTOR inhibitor with a cytotoxic agent.

EXAMPLE 3 p53 (TP53) wild-type A549 and MCF7 cells are seeded at a density of $0.3 \times 10^6$ and $0.4 \times 10^6$ cells/4 ml per 6 cm plates, respectively, and incubated for 24 hours at 37° C. and 5% $CO_2$. Cells are incubated with suboptimal concentrations of cisplatin (e.g. 0.5 to 4 μg/ml) either in combination with 20 nM 40-O-(2-hydroxyethyl) rapamycin or with the vehicle-control DMSO for an additional 24 hours and 30 hours, respectively. Cell extracts corresponding to 30 μg total protein are resolved on 15% SDS-PAGE electrophoresis and immunoblot analysis is performed using mouse monoclonal antibodies raised against p21 (Oncogene Research Products, Clone EA10, catalogue #OP64). In both cell lines, cisplatin alone induces increased p21 protein expression in a concentration-dependent manner. Strikingly, the presence of the mTOR inhibitor, e.g. 40-O-(2-hydroxyethyl) rapamycin, attenuates cisplatin-induced upregulation of p21 protein expression. In contrast, Bax protein expression, a p53-regulated pro-apoptotic protein, is unaffected by either agent alone or in combination. In this assay cytotoxic-induced p21 protein expression is inhibited by the presence of the mTOR inhibitor. This provides an explanation for the enhanced cell killing/apoptotic response observed with cisplatin and mTOR inhibitor combinations.

EXAMPLE 4 p53 (TP53) wild-type A549 cells are seeded at a density of $0.1 \times 10^6$ cells/5 ml per 6 cm plates and incubated for 24 hours at 37° C. and 5% $CO_2$. Cells are left untransfected or transiently transfected with 100 nM siRNA targeting either human p53 (Accession number: NM000546; target sequence: 5'-GCA TCT TAT CCG AGT GGA A-3') or LacZ (Accession number: M55068; target sequence: 5'-GCG GCT GCC GGA ATT TAC CTT-3') control siRNA, using Oligofectamine (Invitrogen, Cat # 12252-011). After 30 hours incubation, cells are incubated with increasing concentrations of cisplatin (e.g. 0.5 to 6 μg/ml) for an additional 24 hours. Cell extracts corresponding to 30 μg (p21) and 50 μg (p53 and PARP) total protein are resolved on 15% (p21) and 10% (p53 and PARP) SDS-PAGE electrophoresis, and immunoblot analysis is performed using mouse monoclonal and rabbit polyclonal antibodies raised against p21 and p53/PARP, respectively. Cisplatin treatment of untransfected or LacZ siRNA control transfected cells induces p53 and p21 protein expression in a concentration-dependent manner, with evidence of PARP cleavage (a marker of apoptosis) at higher cisplatin concentrations (2 to 6 μg/ml). Strikingly, attenuation of cisplatin-induced p53 protein expression occurs in the p53 siRNA transfected cells, which correlates with a dramatic attenuation of p21 expression, PARP cleavage and a loss of cell viability. The same effects on p53 expression, p21 expression and PARP cleavage are also observed with two other siRNA's targeting human p53 (target sequences: 5'-GGA AGA CTC CAG TGG TAA T-3' and 5'-GAT ATT GAA CAA TGG TTC A-3'). These data directly confirm that the enhanced cell killing/apoptotic response observed with cisplatin and mTOR inhibitor combinations are elicited through p53-dependent mechanisms.

EXAMPLE 5 p53 (TP53) wild-type A549 cells are seeded at a density of $0.1 \times 10^6$ cells/5 ml per 6 cm plates and incubated for 24 hours at 37° C. and 5% $CO_2$. Cells are left untransfected or transiently transfected with 100 nM siRNA targeting either p21 (Accession number: NM000389; target sequence: 5'-GTG GAC AGC GAG CAG CTG A-3') or LacZ (as above) control siRNA, using Oligofectamine (Invitrogen, Cat # 12252-011). After 30 hours incubation, cells are incubated with suboptimal concentrations of cisplatin (e.g. 1 to 2 μg/ml) for an additional 24 hours. Cell extracts corresponding to 30 μg (p21) and 50 μg (PARP) total protein are resolved on 15 and 10% SDS-PAGE electrophoresis, respectively, and immunoblot analysis is performed using mouse monoclonal and rabbit polyclonal antibodies raised against p21 and PARP, respectively. Cisplatin treatment of untransfected or LacZ siRNA control transfected cells induces p21 protein expression in a concentration-dependent manner, with little evidence of PARP cleavage (a marker of apoptosis). Strikingly, attenuation of cisplatin-induced p21 protein expression occurs in the p21 siRNA transfected cells, which correlates with a dramatic induction of PARP cleavage. These data directly confirm that attenuation of cytotoxic-induced p21 protein expression is responsible for the enhanced cell killing/apoptotic response observed with cisplatin and mTOR inhibitor combinations.

The invention claimed is:

1. A method of selecting subjects suffering from a proliferative disease for treatment with an mTOR inhibitor and a cytotoxic agent, said method comprising determining the sensitivity of the proliferative disease to the treatment in said subjects by determining the presence of the wild type p53 (TP53) gene, a mutated p53 (TP53) gene, or the absence, deficiency or deletion of the of p53 (TP53) gene and/or the level of expression/post-translational modification of p53 in a sample derived from the subject, and selecting said subjects showing wild-type p53 (TP53) status for treatment.

2. A method according to claim 1, wherein the mTOR inhibitor comprises rapamycin or rapamycin derivative.

3. A method according to claim 2, wherein the rapamycin derivative comprise 40-O-(2-hydroxyethyl) rapamycin, 40-[3-hydroxy-2-(hydroxymethyl)-2-methylpropanoate]-rapamycin or 40-epi-(tetrazolyl)-rapamycin.

4. A method according to claim 1, wherein the cytotoxic agent is selected from an antineoplastic antimetabolite, a platin compound, an alkylating agent, a topoisomerase I or II inhibitor, a microtubule active agent and irradiation.

5. A method for overcoming resistance to a cytotoxic agent in a subject treated with said cytotoxic agent, comprising
   determining the level of p21 expression in a sample derived from the subject,
   if p21 expression is upregulated after administration of an cytotoxic agent, administering to said subject an mTOR inhibitor in combination with the cytotoxic agent,
   determining again the level of p21 expression in a new sample derived from the subject after the treatment with the combination of the mTOR inhibitor and the cytotoxic agent, and
   a p21 expression is downregulated, further treating the subject with the mTOR inhibitor either concomitantly or sequentially with said cytotoxic agent.

* * * * *